United States Patent [19]

Shields et al.

[11] Patent Number: 5,209,242
[45] Date of Patent: May 11, 1993

[54] CONDOMS WITH LEADING SPONGES

[76] Inventors: Jack W. Shields, 1950 Las Tunas Rd., Santa Barbara, Calif. 93103; Richard P. Jobe, 26985 Orchard Hill La., Los Altos Hills, Calif. 94022

[21] Appl. No.: 753,630

[22] Filed: Aug. 30, 1991

[51] Int. Cl.⁵ .......................................... A61F 13/00
[52] U.S. Cl. ..................................... 128/844; 128/842
[58] Field of Search ................................ 604/347–352; 128/842, 844, 913

[56] References Cited

U.S. PATENT DOCUMENTS

| | | |
|---|---|---|
| 2,410,460 | 11/1946 | Robinson ........................ 128/844 X |
| 2,577,345 | 12/1951 | McEwen ............................. 128/844 |
| 3,128,762 | 4/1964 | Young ................................. 128/834 |
| 4,332,243 | 6/1982 | Gutnick . |
| 4,393,871 | 7/1983 | Vorhauer et al. . |
| 4,446,860 | 5/1984 | Gutnick . |
| 4,726,359 | 2/1988 | Schroeder . |
| 4,867,176 | 9/1989 | Lash ............................... 128/844 X |
| 4,972,849 | 11/1990 | Park et al. . |

FOREIGN PATENT DOCUMENTS 2100988  1/1983  United Kingdom ................ 128/844

OTHER PUBLICATIONS

Hatcher et al., "Contraceptive Technology" 15th Revised Edition, (1990) Irvington Publishers, Inc., New York, pp. 159–179.

Department of Health and Human Services Brochure entitled "Condoms and Sexually Transmitted Diseases . . ., Especially AIDS" HHS Publication FDA 90–4239.

*Primary Examiner*—Robert A. Hafer
*Assistant Examiner*—Jam Rimell
*Attorney, Agent, or Firm*—Morrison & Foerster

[57] ABSTRACT

Condoms with leading medication-dispensing sponges surrounding a well for semen at the distal end are described. The purpose is to combine the advantages of condoms and medication-dispensing sponges for reducing the chances of acquiring sexually transmitted diseases, as well as unwanted pregnancy, resulting from sexual intercourse. The sponge, to which medication can be added, will tend to force the medication to the area at which it is most effective.

9 Claims, 3 Drawing Sheets

CONDOMS WITH LEADING SPONGES

BACKGROUND OF THE INVENTION

1. Field of the Invention

Unwanted pregnancies and sexually transmitted diseases (STD), including acquired immune deficiency syndrome (AIDS), are now recognized to be worldwide problems needing superior technological, as well as sociological, approaches to control them.

This invention relates to combining a condom and one or more medication-dispensing sponges to increase the efficiency in the prevention of sexually transmitted diseases (or "STD"), as well as unwanted pregnancies, during coitus.

2. Description of Prior Art

Condoms have been used since the 18th century for preventing STD, as well as unwanted pregnancy (see Hatcher, R.A. et al., *Contraceptive Technology* (1990-1992), Irvington Publishers Inc., NY, 1990). Ninety-nine percent of standard brands of condoms are now made of latex and are supplied with a well for semen at the leading end. Nearly all condoms are approximately 2" wide, 7" long, 0.06-0.08 mm thick, and contain a water-soluble lubricant, such as dry silicone, silicone oil, wet jelly, dry powder or a spermicide. Twelve out of 68 currently produced brands of condoms incorporate ±0.5 gm of nonoxynol-9 on the inner and outer surface where the nonoxynol serves as a lubricant, as well as a detergent which reduces surface tension thereby immobilizing and killing sperm, lymphocytes, and microorganisms which cause some STD.

The routine use of condoms, especially those incorporating nonoxynol-9, particularly during nonmonogamous sexual intercourse was recommended in 1990 (See HHS Publication FDA #90-4239). As a barrier contraceptive, as well as a standard means of preventing STD, condoms have many advantages, including general availability, minimal cost per condom, and a high order of effectiveness. The failure to use a condom, or to use a condom properly, has probably been a greater problem than failure on the part of the condom.

U.S. Pat. No. 4,726,359 to Schroeder discloses a removable protective end cap on a condom to aid in orientation of the condom before use. U.S. Pat. No. 4,972,849 to Park et al. describes a sponge molded into the inside (or penile side) of a condom which sponge might serve various purposes, including the prevention of pregnancy or STD, if containing appropriate medications. Park et al. disclose a slot which allows seminal fluid to pass through the condom and out into the vagina as one of Park's embodiments. This embodiment is ineffective in preventing transmission of AIDS and other STD, as well as of questionable effectiveness in preventing pregnancy.

Condoms have recognized failure rates and other disadvantages. The failure of condoms to prevent pregnancy is rated at ±12% during the first year of use, compared with 13-18% for vaginal diaphragms and cervical caps, 18-28% for contraceptive sponges, and ±21% for spermicides used without adjunctive barriers. The disadvantages of condoms are that: they may break or leak; they may slip off during intercourse or after ejaculation; and they must be taken off immediately after ejaculation before the penis shrinks.

Contraceptive sponges and diaphragms are another popular contraceptive. Natural sea sponges have been used since antiquity for contraception. More recently, open-celled artificial sponges have been used. In 1983, the United States FDA (Food and Drug Administration) approved polyurethane open-cell vaginal contraceptive sponges for use in the United States. The most common form on the market, the TODAY Vaginal Contraceptive Sponge, is a 1.75"×5" pillow-shaped polyurethane sponge that contains 1 gm of nonoxynol-9 spermicide. It has a concave dimple on one side intended to fit over the cervix of the female uterus which decrease the chance of dislodgement during intercourse. The other side of the sponge incorporates a woven polyester loop to facilitate removal of the sponge. The sponge is available in one size, over-the-counter, without prescription. It is moistened with tap water prior to use and inserted deep into the vagina with the concave dimple over the cervix. Once in place, the sponge provides continuous contraceptive protection for up to 24 hours. After use, it is discarded. Its contraceptive effect is exerted by releasing nonoxynol-9 within the sponge, by providing a barrier in front of the cervix, and by trapping sperm within the sponge.

U.S. Pat. No. 4,393,871 to Vorhauer describes a 1 ½ inch diameter, nonoxynol-impregnated "Diaphragm-Disk" with an adhesive coat on one side to line the inside of a diaphragm. U.S. Pat. Nos. 4,332,243 and 4,446,860 to Gutnick describe a burstable medication-releasing well in the wall of a diaphragm or a condom. Gutnick's device depends on the rupture of a partitioning membrane in the wall to release medicament.

Sponges have both advantages and disadvantages to their use. Advantages of contraceptive sponges are that they are easy to buy and use; they can be expected to release increased quantities of water-soluble nonoxynol-9 where most needed in conjunction with intravaginal pressure changes which take place during penile thrusts; they may remain in the vagina after and through more than one episode of coitus; they offer some degree of protection against STD, especially gonorrhea and chlamydia infections; and theoretically offer some protection against other infections, such as genital herpes, trichomonas, syphilis and AIDS. The detergent effect of water-soluble compounds, such as nonoxynol-9, released from the compressed sponges reduces surface tension to the point that motile sperm, lymphocytes, and microorganisms cannot migrate effectively in semen or endocervical secretions.

There are two major disadvantages of contraceptive sponges. They do not necessarily stay where intended, owing to the fact that they have no secure means of retention in front of the cervix of the female uterus. Actually, they are prone to dislocate and rotate, such that they become very difficult for some women to retrieve. Secondly, they are prone to cause endocervical or vaginal irritation, and often foul odor, especially if left in too long. (In addition, the sponge is a relatively expensive form of contraception.)

Thus, although there exist forms of contraceptive devices, i.e. condoms, sponges and diaphragms, which have distinct advantages as both contraceptive and STD prevention methods, these devices also have distinct disadvantages. The devices may either fail to prevent conception, ineffectively prevent STD, and worse, such failures may discourage people from using these important health-protection devices.

SUMMARY OF THE INVENTION

We have discovered that a condom with a sponge permanently attached to its leading end increases the efficiency of either the condom or the sponge alone in contraception, as well as STD prevention. A condom with a leading spermicide, virucide or bacteriocide-releasing sponge surrounding the well for semen is described in order to help prevent STD, as well as unwanted pregnancy. The invention comprises a condom with a leading well for semen, and a medication-releasing sponge at the surface of said leading well.

Our invention is an improvement over the prior art in that the sponge is permanently attached to the outside of a condom on the leading end such that it will be held in an optimal position in front of the os of the female cervix to release medications with pressure changes during heterosexual intercourse. Surrounding the outside of the well for semen in the leading tip of the condom, the sponge can be expected to help prevent breakage of the condom at its weakest point. Moreover, if the condom leaks proximally or slips off, the cervical os and fornices will remain sponge-protected until the condom is removed from the vagina.

DETAILED DESCRIPTION OF THE INVENTION

Figure 1:
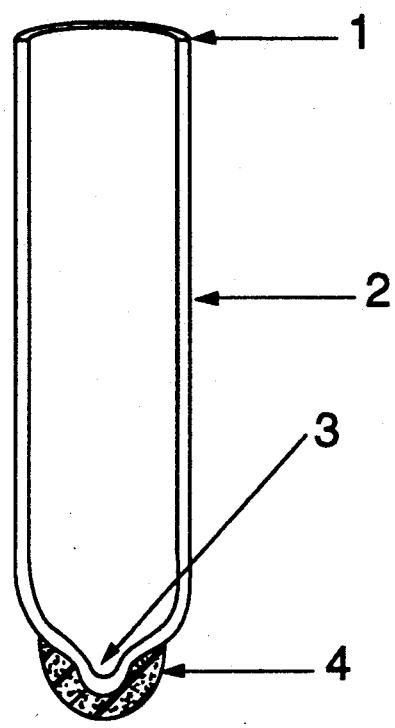
FIG. 1 is a longitudinal section of a condom with a sponge attached to the leading outside surface surrounding the well for semen.

Recognizing some of the advantages, as well as disadvantages, of medication-impregnated contraceptive sponges, Shields U.S. patent application Ser. No. 07/234,812, issuing as U.S. Pat. No. 5,044,376 on 3 Sep. 1991, discloses a reusable vaginal diaphragm and a cervical cap made to securely hold a disposable spermicide-releasing contraceptive sponge directly in front of the uterine cervix. The contents of the foregoing Shields application, and all other art references cited throughout this disclosure, are herein incorporated by reference.

The present invention has several advantages over prior art condoms. One advantage of the invention is its ability to provide additional barriers to impede the migration of sperm, lymphocytes and microorganisms in semen. The invention is also able to apply and hold a medication-dispensing sponge where it is most effective, near the opening of the female uterine cervix, especially in the event the condom tears, leaks or breaks during coitus.

Another advantage of the invention is its ability to hold a contraceptive sponge in a position such that penile thrusts during conventional vaginal intercourse will exert maximal pressure on the sponge, causing soluble medications to be released in optimal concentrations. Because the condom holds the sponge in position when it is most needed, i.e. during sexual intercourse, irritation of the endocervix and vagina by the sponge or sponge contents during periods of sexual inactivity is minimized. Because the condom holds the sponge in a position where it is most needed, i.e. near the cervical os where the epithelial layer is thinnest and therefore most vulnerable to transmission of AIDS and other STD, the modified condom of the present invention has distinct advantages over the prior art.

Another advantage of the invention is its ability to provide an effective chemical, as well as physical barrier to the sharing of male semen and female endocervical secretions which might be infectious to either sexual partner during coitus. The condom provides a physical and chemical barrier system which is simple, inexpensive, not messy, and just as easy and pleasurable to use as an unmodified condom during sexual intercourse. A final advantage of the invention is to provide an element of friction in the penile thrust to be perceived by the female partner as a more skin-like surface of the penis and condom.

As used herein, the term "medication" includes compounds that have spermicidal, virucidal, cytocidal, antimicrobial, and antifungal effects. The medication can be used alone or in combination with other known medications. The medication may be known contraceptive compounds, such as nonoxynol-9, which is disclosed in U.S. Pat. No. 2,541,103, or other such compositions known in the art.

The modified condom can be manufactured in various sizes, to minimize slippage, minimize tearing and maximize comfort during use. Manufactured condoms can be modified by attaching sponges to their ends.

Alternatively, the manufacturing process of the condom is modified so that a sponge is incorporated into the outside leading end of the condom at the time of its manufacture. The sponge can be first attached and then infused with medication, such as nonoxynol-9. Alternatively, a sponge that already contains medication can be attached to an already manufactured condom or incorporated into the condom during manufacture. The completed condoms are preferably individually packaged in accordance with standard packaging techniques.

The shape of the sponge may be modified to provide a variety of shapes and sizes. For example, a large sponge might increase user pleasure and increase use of the device. A broad sponge might prevent premature ejaculation. A variety of different sponges or sponge-like materials may be used and will affect shape, texture, and size of the parts.

A second sponge may be provided inside the condom to provide chemical or adsorptive action against the sperm such that if the condom breaks or slips off too soon the adverse effects of the semen have already been neutralized to some extent. The second sponge thus can hold the semen and medications.

The shaft of the condom will generally be configured like standard condoms, i.e, having a smooth surface. Alternative embodiments, such as ribs, colors, flavors, fragrances, and other "novelty" forms of condoms may be manufactured according to the present invention.

EXAMPLES

As shown in FIG. 1, the modified condom consists of a proximal ring (1) having adequate elasticity for comfortable use and a shaft (2) which, in the preferred embodiment, are made in at least three sizes, a well (3) for semen, and a securely attached sponge (4) surrounding the outside surface of the well and, in some embodiments, also the shaft.

Figure 2:
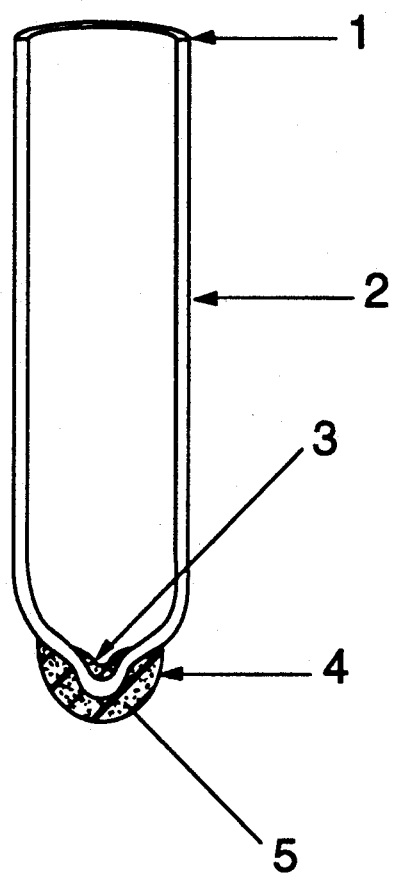
FIG. 2 is a longitudinal section of a condom with a sponge attached to both the leading outside and inside walls surrounding the well for semen.

In a second embodiment, shown in FIG. 2, a second sponge (25), not necessarily of the same kind or content, is securely attached to the inside surface of the well for semen (3) in order to reinforce the thin, but impervious layer which forms the well at the leading end of the condom and to prevent shearing. The inside sponge might be specialized for improved trapping of sperm or maintaining adequate lubrication inside the condom, and may contain medications to neutralize the sperm or bacterial or viral entities that cause STD.

Figure 3:
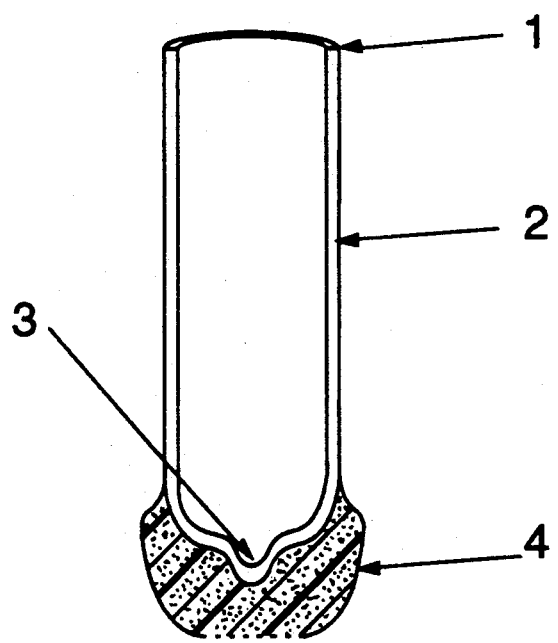
FIG. 3 is a longitudinal section of a condom with a sponge that is shaped similar to a glans penis and corona at the leading outside surface of the condom.

In a third embodiment, shown in FIG. 3, the sponge (4) is shaped similar to a glans penis and surrounding corona.

The condom can be manufactured by readily modifying known techniques. As disclosed, for example, in U.S. Pat. No. 4,972,849, a steel or ceramic mandrel of predetermined size and phallic shape is dipped into a bath containing a liquid condom material, e.g., latex or silicone. Any convenient means can be used to affix the sponge to the condom. The sponge could, for example, be placed on the mandrel before it is dipped. After dipping, the condom can be turned inside out so that the sponge is on the outside of the condom. Alternatively, the sponge can be attached using an adhesive, or can be attached to the condom when the condom is not yet solidified. Alternatively, the sponge can be attached in a manner similar to the Shields application, Ser. No. 07/234,812 supra.

The sponge can contain spermicide or other medication at the time that it is affixed to the condom. Alternatively, spermicide or other medication may be added to the sponge by the user.

A thickened ring is typically formed at the upper (open) end of the condom during manufacture. Lubricant and/or spermicide may then be added to the modified condom. The condom is rolled off the mandrel around the thickened ring and packaged.

Although the modified condom has been described partly in terms of specific embodiments, these embodiments are exemplary only, and not intended to be limiting. Drawings are of a simple form among many possibilities as the shape, size and volume of the sponge (with or without additional sponges inside the condom), can take many forms which would depend upon materials used, concentration and coverage of agent added for spermicidal or microbial effect. It will be appreciated by those skilled in the art that wide variation in details can be made without departing from the spirit of the claimed invention.

We claim:

1. A condom comprising a proximal ring, a tubular shaft and a closed leading end wherein said closed leading end further comprises a sponge on the outside surface of said leading end wherein the sponge is capable of holding medications, which are released during coitus, wherein the condom further includes a leading well and said sponge is located on the exterior surface of said well.

2. The condom of claim 1, wherein the medication is a spermicide.

3. The condom of claim 2, wherein the spermicide is nonoxynol-9.

4. The condom comprising a proximal ring, a tubular shaft and a closed leading end wherein said closed leading end further comprises a sponge on the outside surface of said leading end wherein the sponge is capable of holding medications, which are released during coitus, wherein the condom further includes a leading well and said sponge is located on both the interior and exterior surfaces of said well.

5. The condom of claim 1, wherein the sponge is generally configured to resemble a glans penis and a corona.

6. The condom of claim 1, wherein the shaft is textured.

7. A method of making a modified condom comprising providing a condom comprising a proximal elastic ring, a tubular shaft and a closed leading end which end further includes a leading well;
   providing first and second sponges;
   and appending the first sponge to the interior surface of said closed leading end and well and said second sponge to the exterior surface of said closed leading end and well.

8. The method of claim 7, wherein the sponge is generally configured to resemble a glans penis and a corona.

9. The method of claim 7, wherein the tubular shaft is textured.

* * * * *